United States Patent [19]

Chang et al.

[11] Patent Number: 4,963,495

[45] Date of Patent: Oct. 16, 1990

[54] SECRETION OF HETEROLOGOUS PROTEINS

[75] Inventors: Chung N. Chang, San Mateo; Gregory L. Gray, San Francisco; Herbert L. Heyneker, Burlingame; Michael W. Rey, San Mateo, all of Japan

[73] Assignee: Genentech, Inc., San Francisco, Calif.

[21] Appl. No.: 658,342

[22] Filed: Oct. 5, 1984

[51] Int. Cl.$^5$ .................. C10P 21/00; C12N 12/00
[52] U.S. Cl. .................. 435/320; 536/27; 935/47; 935/48; 435/172.3
[58] Field of Search .................. 935/40, 41, 47, 48; 435/68, 253, 172.3, 17, 320; 536/27, 3

[56] References Cited

U.S. PATENT DOCUMENTS

| | | | |
|---|---|---|---|
| 4,338,397 | 7/1982 | Gilbert et al. | 435/68 |
| 4,375,514 | 3/1983 | Siewert et al. | 435/172 |
| 4,411,994 | 10/1983 | Gilbert et al. | 435/71 |
| 4,711,844 | 11/1987 | Chang | 435/320 |

FOREIGN PATENT DOCUMENTS

| | | |
|---|---|---|
| 0055942 | 7/1982 | European Pat. Off. . |
| 007569 | 4/1983 | European Pat. Off. ............. 935/41 |
| 0146958 | 8/1984 | European Pat. Off. . |
| 0121352 | 10/1984 | European Pat. Off. . |
| WO84/00774 | 3/1984 | PCT Int'l Appl. . |
| 2091268 | 7/1982 | United Kingdom . |

OTHER PUBLICATIONS

Bassford, P. J., Jr., T. J. Silhavy, and J. R. Beckwith, *Journal of Bacteriology* 139 (1):19–31 (1979).
Ghrayeb, J., H. Kimura, M. Takahara, H. Hsiung, Y. Masui, and M. Inouye, *EMBO J* 3:2437–2442 (1984).
Goeddel, D. V., H. L. Heyneker, T. Hozumi, K. Itakura, D. G. Yansura, M. J. Ross, G. Miozzari, R. Crea and P. H. Seeburg, *Nature*, 281:544–548 (1979).
Oka, T., et al., *Proc. Natl. Acad. Sci. U.S.A.* 82:7212–7216, 1985.
Ikehara, M. et al., *Proc. Natl. Acad. Sci. USA* 81:5956–5960, 1984.
K. Talmadge et al., "P.N.A.S. USA" 77(6):3369–3373 (Jun. 1980).
K. Talmadge et al., "P.N.A.S. USA" 77(7):3988–3992 (Jul. 1980).
O. Zemel-Dreasen et al., "Gene" 27: 315–322 (1984).
J. Kadonaga et al., "J. Biol. Chem." 259(4):2149–2154 (1984).
K. Ohsuye et al., "Nucl. Acid Res." 11(5):1283–1294 (1983).
T. Silhavy et al., "Microb. Reviews" 47(3):313–344 (Sep. 1983).
G. Gray et al., "Biotech." 161–165 (Feb. 1984).
I. Palva et al., "Gene" 22:229–235 (1983).
S. Michaelis et al., "J. Bact." 154(1):366–374 (Apr. 1983).
H. Inouye et al., "J. Bact." 149(2):434–439 (Feb. 1982).
H. Inouye et al., "J. Bact." 146(2):668–675 (May 1981).
R. Picken et al., "Infection and Immunity" 42(1) 269–275 (Oct. 1983).
T. Taniguchi et al., "P.N.A.S. USA" 77(9):5230–5233 (Sep. 1980).

*Primary Examiner*—Robin L. Teskin
*Attorney, Agent, or Firm*—Robert H. Benson; Max D. Hensley

[57] ABSTRACT

Direct linkage of DNA encoding prokaryotic signals such as *E. coli* enterotoxin with DNA encoding mature eukaryotic proteins followed by transformation and culture of bacterial hosts characterized by a periplasmic space, yields substantial amounts of periplasmic mature protein.

4 Claims, 18 Drawing Sheets

THE ST II GENE

```
TAAATACCTACAACGGGTGATTGACACTACACTCATTAACTATACTGCAAGTAGCATTAAAAATCTTAATAAAGGAGAGC
1           20              40              60              80
                  -35                                              -10              MnII    S.D.
TTCGTCACATTTTTTGACTTGACTCATCATATAAAAGCCCACTGGTATAAGTTTATTGCTTATAGCAATAAGGTTGAGGTG
                  100             120             140             160
                                                                  -10
          met lys lys asn ile ala phe leu leu ala ser met phe val phe ser ile ala
          ATG AAA AAG AAT ATC GCA TTT CTT CTT GCA TCT ATG TTC GTT TTT TCT ATT GCT
                                  180                     200
          -20
                                                                                  10
          -1 cleavage site
thr asn ala tyr ala SER THR GLN SER ASN LYS LYS ASP LEU CYS GLU HIS TYR ARG GLN
ACA AAT GCC TAT GCA TCT ACA CAA TCA AAT AAA AAA GAT CTG TGT GAA CAT TAT AGA CAA
220                     240                     BgIII 260
                        20                                              30
ILE ALA LYS GLU SER CYS LYS LYS GLY PHE LEU GLY VAL ARG ASP GLY THR ALA GLY ALA
ATA GCC AAG GAA AGT TGT AAA AAA GGT TTT TTA GGG GTT AGA GAT GGT ACT GCT GGA GCA
280                     300                     320   RsaI
                        40
CYS PHE GLY ALA GLN ILE MET VAL ALA ALA LYS GLY CYS OC
TGC TTT GGC GCC CAA ATA ATG GTT GCA GCA AAA GGA TGC TAA TATATTTATCAATAGCATTCAGCA
340                     360                     380                     400
CCATATACACAAAAATAATTTTTCATAAAAGAACTCTATAAAATAAATATTTTTGTGACAATGTCCTAACGCAAGACG
                  420             440             460             480
GACATTGTCCATTCTCACTGCAGGTAAATGATCTGTAATAGTC
                  500   PstI        520
```

Fig.1.

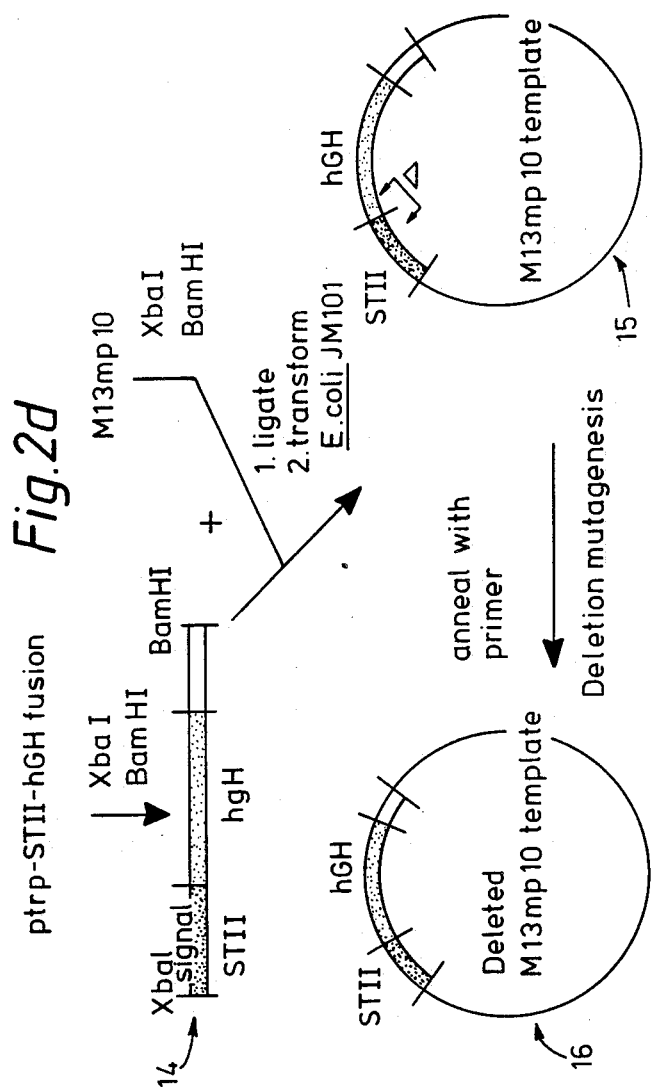

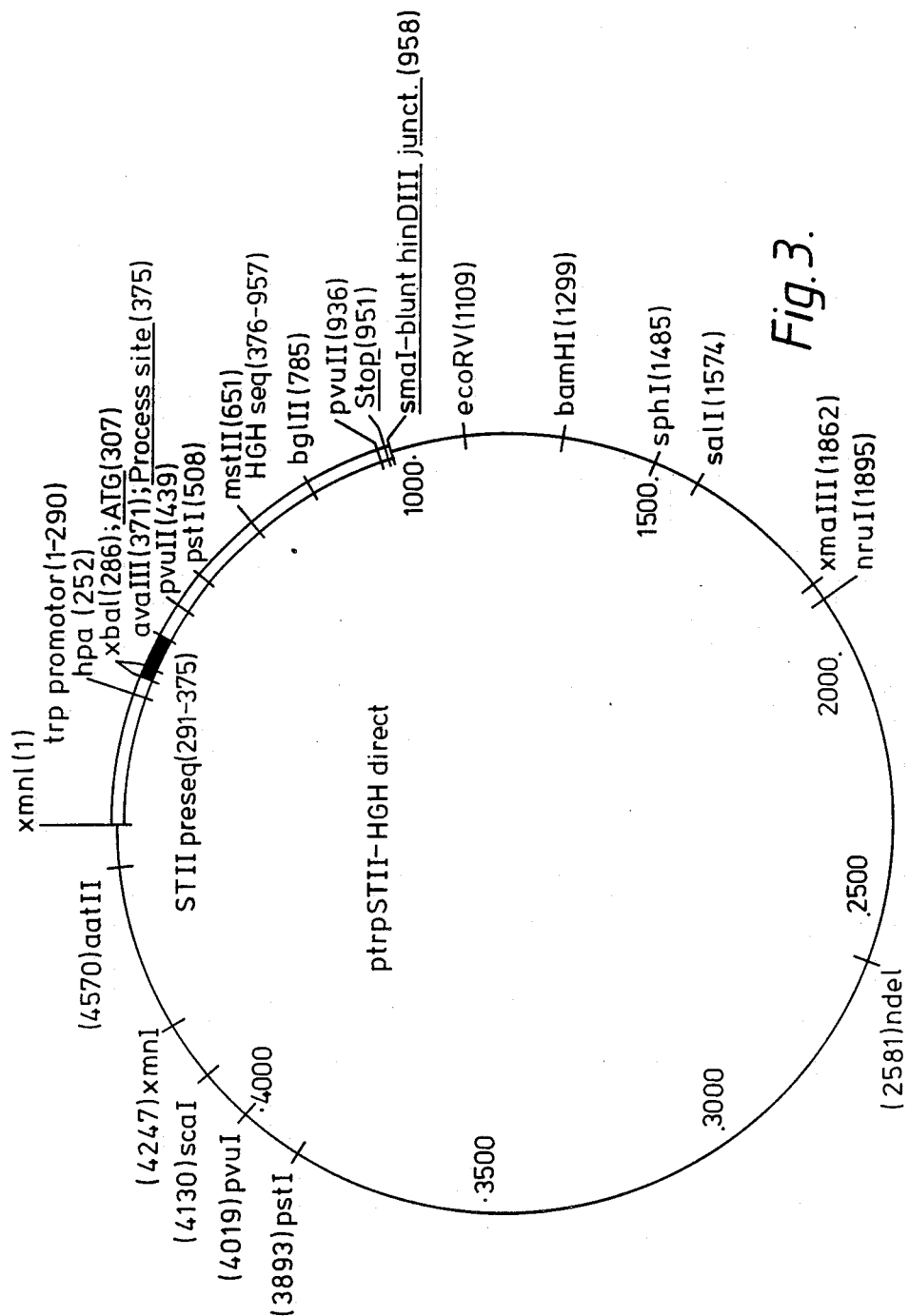

```
                                                                                              ← Trp promoter
AATTCATGCTGTGTGGTGTCATGTCGGTGATCGCCAGGGTGCCGACGCGCATCTCGACTGCACGATGCAGGCAGGTCACCAATGCTTCTGGCCTGTCAGGCAGCCAATCGGAAGCTGTGGTATGGCTGTGC AGGTCGTAAATCACTGCATAATTCGTGTCGCTCAAGGCGCACTCCCGTTCTGGATAATGTTTTTTGCGCCGACATCATAACGGTTCTGGCAAATATTCTGAAATGAGCTGTTGACAATT
                                                                                                            -23                -20
                      trp S.D.          STII S.D.                                         met lys lys asn ile ala phe leu ala ser met
AATCGAACTAGTTAACTAGTACGCAAGTTCACGTAAAAAGGGTATCTAGAGAGGTTGAGGTGATTTT                       ATG AAA AAG AAT ATC GCA TTT CTT GCA TCT ATG
                                                                 xbaI
                                                                    1                                        10
phe val phe ser ile ala thr asn ala tyr ala phe pro thr ile pro leu ser arg  phe asp asn ala met leu arg ala his arg
TTC GTT TTT TCT ATT GCT ACA AAT GCC TAT GCA TTC CCA ACT ATA CCA CTA TCT CGT  TTC GAT AAC GCT ATG CTT CGT GCT CAT CGT
                                                                                          40
 20                                      30
leu his gln leu ala phe asp thr tyr gln leu phe glu glu phe asp  lys tyr ser phe leu gln asn pro gln
CTT CAT CAG CTG GCC TTT GAC ACC TAC CAG GAG TTT GAA GAA TTC GAT  AAG TAT TCA TTC CTG CAG AAC CCC CAG
                                                                                   70
 50                            60
thr ser leu cys phe ser glu ser ile pro ser asn arg glu glu thr gln gln  lys ser asn leu glu leu arg ile ser
ACC TCC CTC TGT TTC TCA GAG TCT ATT CCG TCC AAC AGG GAG GAA ACA CAG  AAA TCC AAC CTA GAG CTC CGC ATC TCC
                                                                                           100
 80                                      90
leu leu ile gln ser trp leu glu pro val gln phe leu arg ser val  phe ala asn ser leu val tyr gly ala ser asp ser asn
CTG CTC ATC CAG TCG TGG CTG GAG CCC GTG CAG TTC CTC AGG AGT GTC  TTC GCC AAC AGC CTA GTG TAC GGC GCC TCT GAC AGC AAC
                                                                                    130
110                                      120
val tyr asp leu leu lys asp leu glu glu gly ile gln thr leu met gly arg  leu glu asp gly ser pro arg thr gly ile phe
GTC TAT GAC CTC CTA AAG GAC CTA GAG GAA GGG ATC CAA ACG CTG ATG GGG  AGG CTG GAA GAT GGC AGC CCC CGG ACT GGG ATC TTC
                                                                                           160
140                                      150
lys gln thr tyr ser lys phe asp thr asn ser his asn asp asp ala  leu leu lys asn tyr gly leu leu tyr cys phe arg lys asp
AAG CAG ACC TAC AGC AAG TTC GAC ACA AAC TCA CAC AAC GAT GAC GCA  CTA CTC AAG AAC TAC GGG CTG CTC TAC TGC TTC AGG AAG GAC
                                                                                           pBR322
170                                                  190 191
met asp lys val glu thr phe leu arg ile val gln cys arg ser val glu gly ser cys gly phe AM
ATG GAC AAG GTC GAG ACA TTC CTG CGC ATC GTG CAG TGC CGC TCT GTG GAG GGC AGC TGT GGC TTC TAG CTGCCCTTAATGCGCTAGTTTATCACAGTT
                                                                                                      SmaI-Blunt HindIII junction STII S-D Seq.      GGTTGAGGTGATTT
StII Leader Seq.   -23 to -1
Mature HGH Seq.    1-191
```

*Fig.3A.*

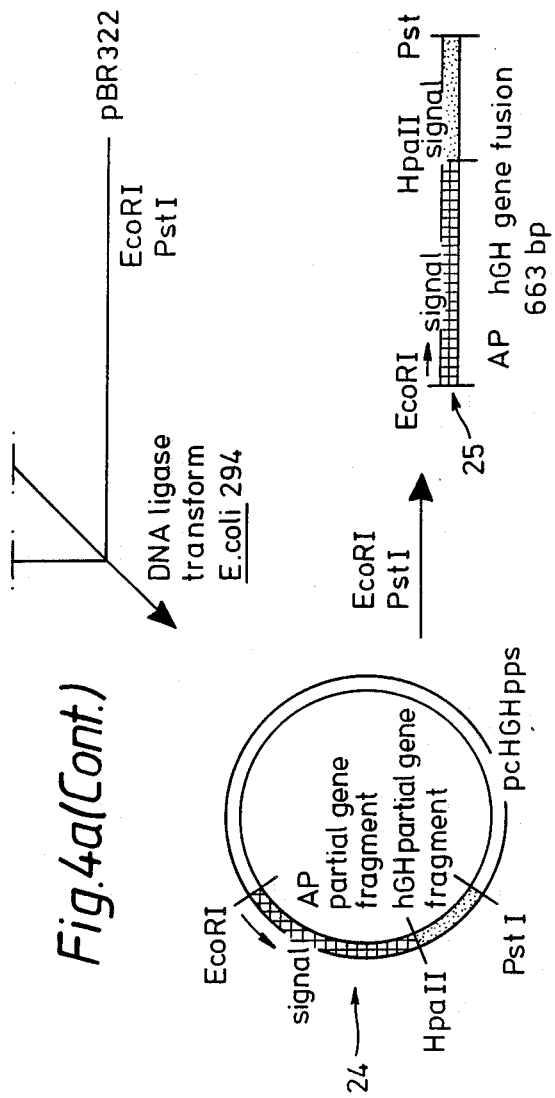

```
GAATTCAACTTCTCCATACTTTGGATAAGGAAAATACGAGACATGAAAAATCTCATTGCTGAGTTGTTATTTAAGCTTGCC

CAAAAGAAGAGAGTCGAAAGAACTGTGTGCGCAGGTAGAAGCTTTGGAGATTATCGTCACTGCAATGCTTCGCAATA

TGGCGCAAAATGACCAACACGGTTGATCAGGTAGAGGGGCGCTGTACGAGGTAAAGCCCGATGCCAGCATTCC

TGACGACGATACGGAGCTGCTGCCGATTACGTAAAGAAGTTATTGAAGCATCCTCGTCAGTAAAAAGTTAATCTTTTC

AACAGCTGTCATAAGTTGTCACGGCCGAGACTTATAGTCGCTTTGTTTTTATTTTTAATGTATTGTAACTAGTACG
                trp S.D.        STII S.D.         -23          met lys lys asn ile ala phe leu leu
CAAGTTCACGTAAAAAGGGTATCTAGAAGGTTGAGGTGATTTT ATG AAA AAG AAT ATC GCA TTT CTT CTT
                          xbaI
                                                         -20                      1
ala ser met phe val phe ser ile ala thr asn ala tyr ala phe pro thr ile pro leu
GCA TCT ATG TTC GTT TTT TCT ATT GCT ACA AAT GCC TAT GCA TTC CCA ACT ATA CCA CTA
             -10                                                            20
ser arg leu phe asp asn ala met leu arg ala his arg gln leu ala phe asp
TCT CGT CTA TTC GAT AAC GCT ATG CTT CGT GCT CAT CGT CAT CAG CTG GCC TTT GAC
                 10                                              40
thr tyr gln glu phe glu glu ala tyr ile pro lys glu gln lys tyr ser phe leu gln
ACC TAC CAG GAG TTT GAA GAA GCC TAT ATC CCA AAG GAA CAG AAG TAT TCA TTC CTG CAG
                       30
```

Fig. 5.

```
            50                   60                   70                   80
asn pro gln thr ser cys phe ser glu ser ile pro thr pro ser asn arg glu glu
AAC CCC CAG ACC TCC TGT TTC TCA GAG TCT ATT CCG ACA CCC TCC AAC AGG GAG GAA thr gln gln lys ser asn leu glu leu leu arg ile ser leu leu ile gln ser trp
ACA CAA CAG AAA TCC AAC CTA GAG CTG CTC CGC ATC TCC CTG CTC ATC CAG TCG TGG
            70                   80                   90                  100
leu glu pro val gln phe leu arg ser val phe ala asn ser leu val tyr gly ala ser
CTG GAG CCC GTG CAG TTC CTC AGG AGT GTC TTC GCC AAC AGC CTA GTG TAC GGC GCC TCT
            90                  100                  110                  120
asp ser asn val tyr asp leu leu lys asp leu leu glu glu gly ile gln thr leu met gly
GAC AGC AAC GTC TAT GAC CTC CTA AAG GAC CTA GAG GAA GGC ATC CAA ACG CTG ATG GGG
            110                 120                  130                  140
arg leu glu asp gly ser pro arg thr gly gln ile phe lys gln thr tyr ser lys phe
AGG CTG GAA GAT GGC AGC CCC CGG ACT GGG CAG ATC TTC AAG CAG ACC TAC AGC AAG TTC
            130                 140                  150                  160
asp thr asn ser his asn asp asp ala leu leu lys asn tyr gly leu leu tyr cys phe
GAC ACA AAC TCA CAC AAC GAT GAC GCA CTA CTC AAG AAC TAC GGG CTG CTC TAC TGC TTC
            150                 160                  170                  180
arg lys asp met asp lys val glu thr phe leu arg ile val gln cys arg ser val glu
AGG AAG GAC ATG GAC AAG GTC GAG ACA TTC CTG CGC ATC GTG CAG TGC CGC TCT GTG GAG
            170                      pBR322
gly ser cys gly phe   AM
GGC AGC TGT GGC TTC   TAG CTGCCCTTAATGCGGTAGTTTATCACAGTT
190 191                            SmaI-Blunt HindIII junction
```

Fig.5(Cont.)

```
GAATTCAACTTCTCCATACTTTGGATAAGGAATACAGACATGAAAAATCTCATTGCTGAGTTGTTATTTAAGCTTGCC
CAAAAGAAGAAGAGTCGAAAGAACTGTGTGCCGCAGGTAGAAGCTTTGGAGATTATCGTCACTGCAATGCTTCGCAATA
TGGCGCAAAATGACCAACAGCGGTTGATTGATCAGGTAGAGGGGGCGCTGTACGAGGTAAAGCCCGATGCCAGCATTCC
TGACGACGATACGGAGCTGCTGCGCGATTACGTAAAGAAGTTATTGAAGCATCCTCGTCAGTAAAAGTTAATCTTTTC
                                                         AP -    SD
AACAGCTGTCATAAAGTTGTCACGGCCGAGACTTATAGTCGCTTGTTTTTATTTTTAATGTATTTGTACATGGAGAA
              -21 -20                                         -10
              met lys gln ser thr ile ala leu leu pro leu phe thr pro val
       AATAAA GTG AAA CAA AGC ACT ATT GCA CTG GCT CTC TTA CCG TTT ACC CCT GTG 1                                        10
       thr lys ala phe pro thr ile pro leu ser arg leu phe asp asn ala met leu arg ala
       ACA AAA GCC TTC CCA ACT ATA CCA CTA TCT CGT CTA TTC GAT AAC GCT ATG CTT CGT GCT 20                              30
       his arg leu his gln leu ala phe asp thr tyr gln phe glu glu ala tyr ile pro
       CAT CGT CTT CAT CAG CTG GCC TTT GAC ACC TAC CAG GAG TTT GAA GAA GCC TAT ATC CCA 40                              50
       lys glu gln lys tyr ser phe leu gln asn pro gln thr ser leu cys phe ser glu ser
       AAG GAA CAG AAG TAT TCA TTC CTG CAG AAC CCC CAG ACC TCC CTC TGT TTC TCA GAG TCT
```

Fig. 6.

```
                                        60                                       70
ile pro thr pro ser asn arg glu glu thr gln gln lys ser asn leu glu leu arg
ATT CCG ACA CCC TCC AAC AGG GAG GAA ACA CAA CAG AAA TCC AAC CTA GAG CTG CGC 80                                       90
ile ser leu leu ile gln ser trp leu glu pro val gln phe leu arg ser val phe
ATC TCC CTG CTC ATC CAG TCG TGG CTG GAG CCC GTG CAG TTC CTC AGG AGT GTC TTC 100                                      110
ala asn ser leu val tyr gly ala ser asp ser asn val tyr asp leu lys asp leu
GCC AAC AGC CTA GTG TAC GGC GCC TCT GAC AGC AAC GTC TAT GAC CTC AAG GAC CTA 120                                      130
glu glu gly ile gln thr leu met gly arg leu glu asp gly ser pro arg thr gly gln
GAG GAA GGC ATC CAA ACG CTG ATG GGG AGG CTG GAA GAT GGC AGC CCC CGG ACT GGG CAG 140                                      150
ile phe lys gln thr tyr ser lys phe asp thr asn ser his asn asp asp ala leu leu
ATC TTC AAG CAG ACC TAC AGC AAG TTC GAC ACA AAC TCA CAC AAC GAT GAC GCA CTA CTC 160                                      170
lys asn tyr gly leu leu tyr cys phe arg lys asp met asp lys val glu thr phe leu
AAG AAC TAC GGG CTG CTC TAC TGC TTC AGG AAG GAC ATG GAC AAG GTC GAG ACA TTC CTG 180                                   190 191
arg ile val gln cys arg ser val glu gly ser cys gly phe AM
CGC ATC GTG CAG TGC CGC TCT GTG GAG GGC AGC TGT GGC TTC TAG CTGCCC
```

*Fig.6(Cont.)*

SECRETION OF HETEROLOGOUS PROTEINS

Reference is made to related copending U.S. Ser. No. 658,095 now abandoned and U.S. Ser. No. 658,339 now abandoned allowed U.S. Pat. No. 4,680,262, both filed of even data.

This application relates to the synthesis of mature eukaryotic proteins in bacterial hosts. It is directed to providing vectors that will express hybrid preproteins in high yields in host cells, cleave the signal sequence from the preprotein and secrete mature eukaryotic protein in the periplasmic space of the host cells.

Literature that should be consulted in regard to this application is U.S. patent Nos. 4,375,514 and 4,411,994; U.K. patent application 2,091,268A (published 1982); I. Palva et.al., "Gene" 22: 229-235 (1983); H. Inouye et al., "J. Bact" 148(2): 434-439 (1983); K. Talmadge et al., "P.N.A.S. USA" 77(7): 3988-3992 (1980); K. Talmadge et al., "P.N.A.S. USA" 77(6): 3369-3373 (1980); European Patent Application 114,695; R. Picken et al., "Infection and Immunity" 42(1): 269-275 (1983); T. Silhavy et al., "Microbiological Reviews" 47(3): 313-344 (September 1983); J. Kadonaga et al., "J. Biol. Chem." 259(4): 2149-2154 (February 1984); International PCT application WO 84/00774 (March 1984); O. Zemel-Dreasen et al., "Gene" 27: 315-322 (1984); S. Michaelis et al., "J. Bact." 154(1): 366-374 (April 1983); European Patent Application 114,695 (published August 1, 1984); and G. Gray et al., "Biotechnology" pp 161-165 (February 1984).

Secretion of mature eukaryotic protein into the periplasm of gram negative bacteria such as *E. coli* has been an objective of the art for a number of years. Periplasmic secretion is a desirable objective because the product is thereby compartmentalized between the inner and outer membranes of the cultured cells and not exposed to the rigors of the extracellular medium. Exposure to these rigors, e.g., dilution, unfavorable salts or pH, and proteases, has handicapped the commercialization of nonperiplasmic secretion systems such as those using Bacillus or yeast. Also, periplasmic compartmentalization simplifies purification of the desired mature eukaryotic protein.

Many naturally occurring secretory and membrane proteins are initially synthesized as nascent or intracellular preproteins. These are proteins in which a "signal" polypeptide is linked to the amino acid residue that will become the amino terminus of the mature protein upon secretion. The signal polypeptide is a peptide sequence which enables the mature protein to pass through the cellular membrane of the cell. The signal peptide is cleaved away, or "processed", in passing through the cellular membrane by a mechanism that is under study. If the processing occurs properly the mature protein will be free of any amino terminal extraneous signal amino acid residues and will have the proper amino terminal amino acid. Thus, if a heterologous gene which includes the DNA encoding a signal sequence is expressed by a host gram negative bacterial cell and the signal is then cleaved properly by the host, . the mature protein without an appended methionine moiety is secreted into the periplasmic space of the host, i.e., the space between the inner, or cytoplasmic, membrane and the outer membrane of the host.

Heretofore the vector constructions employed for periplasmic secretion in gram negative bacteria have, to applicants' knowledge, all entailed the use either of complete eukaryotic signals or of partial hybrids. Constructions which encode two typical partial hybrids are schematically shown below.

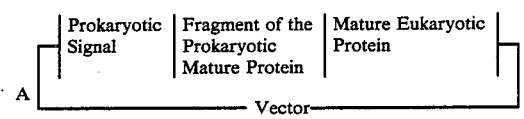

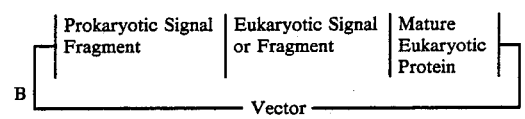

Constructions like the partial bacterial preprotein-mature eukaryotic protein fusions shown in schematic A result in the secretion of fusions of the prokaryotic and eukaryotic proteins. It is inconvenient and sometimes impossible to remove the extraneous amino terminal amino acids encoded by the prokaryotic DNA. On the other hand, constructions like those of schematic B, result in the secretion of mature protein but yields of secreted mature eukaryotic protein are less than desired. It would be useful to construct hybrid vectors as described below which could be expressed as direct hybrids of the prokaryotic signal and mature eukaryotic protein, processed by hosts and secreted into the periplasm. Such a vector is shown below.

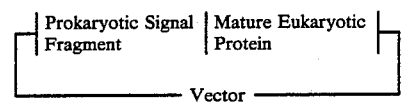

J. Kadonaga et al., op cit, prepared a vector of the direct hybrid type in which the beta lactamase signal was linked directly to DNA for mature chicken triose phosphate isomerase. However, the isomerase was apparently neither secreted nor processed but resided as a hybrid protein both free in the cytoplasm and attached to the cytoplasmic side of the inner membrane. These authors concluded that the amino acid sequence of at least the early part of a mature secreted bacterial protein is critical to secretion across the inner membrane of *E. coli.*

The reasons for the relative difficulty previously encountered in obtaining the secretion of the product of direct hybrids are unknown. However, applicants speculate that while secretion and processing machinery are conserved in bacteria (so that eukaryotic preproteins have been processed in several cases), or the machinery is somewhat flexible (as shown in processing of schematic A-type fusions), a particularly difficult obstacle to secretion would appear to be posed by constructions in which such bacteria must process the expressed product at a completely artificial cleavage site, i.e., a site which is neither a prokaryotic nor eukaryotic site for about from 1 to 3 residues on either side of the point at which hydrolysis occurs. Contrary to this expectation, and the prior failures and skepticism of those skilled in the art, applicants have found that periplasmic bacteria indeed can process direct fusions of prokaryotic signals with mature eukaryotic proteins, and can do so with secreted mature protein yields higher than those obtained by applicants with eukaryotic preproteins. Particularly satisfactory results have been obtained in secreting mammalian growth hormones.

Mammalian growth hormone is a normal product of the pituitary gland. Mammalian growth hormones are now known to exhibit. a degree of species cross-specificity, a function of similar amino acid sequence and conformation. Human growth hormone (hGH) consists of 191 amino acids and has a molecular weight of about 21,500. HGH is in clinical use for the treatment of hypopituitary dwarfism. It also has been proposed to be effective in the treatment of burns, wound heating, dystrophy, bone knitting, diffuse gastric bleeding and pseudoarthrosis.

Recently, hGH has been synthesized in recombinant host cells. See, for example, U.S. Pat. No. 4,342,832. HGH is not significantly degraded by bacterial cells and can be produced directly if the gene for its direct expression, including the appropriately placed start codon, is linked to a suitable promoter. Because prokaryotes frequently do not remove the amino-terminal methionine from the resulting protein, expression of heterologous hGH DNA under control of a bacterial promoter as shown in U.S. Pat. No. 4,342,832 yields hGH having methionine as its first amino acid. The reason for this is that the DNA ATG codon (start codon) is ultimately expressed as methionine. Results to date, for example, with production of hGH in E. coli, have shown that the host cell has only a limited intracellular ability to cleave methionine from hGH and only limited techniques presently exist to do so in vitro.

Copending U.S. Pat. No. 488,232 now U.S. Pat. No. 4,755,465, filed Apr. 25, 1983 provides for the synthesis and secretion of mature hGH in prokaryotic hosts by transforming such hosts with prehGH, i.e., with hGH having its normal eukaryotic signal sequence. Host cells were able to express prehGH, to recognize the eukaryotic signal and to process the preprotein properly. Mature hGH was then recovered from the periplasm, but yields were not as high as desired.

Accordingly, it is an object herein to express and secrete high periplasmic amount of mature eukaryotic protein in bacterial hosts.

It is a further object to obtain periplasmic mature human growth hormone in elevated amounts.

It is another object to provide prokaryotic signal polypeptides capable of facilitating the expression and secretion of eukaryotic proteins.

SUMMARY

Mature eukaryotic protein is expressed and secreted in the periplasmic space of a host organism by a method comprising
  (a) constructing a vector for expressing a secretable direct hybrid, which vector contains DNA encoding a prokaryotic secretion signal sequence linked at its 3' end to the 5' end of DNA encoding the mature protein;
  (b) transforming the prokaryotic host organism with the vector of step (a);
  (c) culturing the transformed host of step (b); and
  (d) allowing mature protein to collect in the periplasm of the host.

A DNA sequence is provided which encodes a periplasmic bacterial secretion signal sequence linked at its 3' end to the 5' end of DNA encoding a mature eukaryotic protein other than chicken triose phosphate isomerase. The DNA encoding E. coli enterotoxin signals are particularly useful in this regard. This signal DNA is characterized by not being linked (a) at its 3' end to the 5' end of DNA encoding mature enterotoxin or (b) at its 5' end to the 3' end of the enterotoxin promoter. It is conveniently employed as a cassette in the construction of enterotoxin signal-containing vectors. A preferred enterotoxin is STII.

The STII Shine-Dalgarno (S.D.) sequence is a particularly powerful ribosome binding site which contributes to yield improvement. It ordinarily is linked to prokaryotic promoters such as the tryptophan (trp) or bacterial alkaline phosphatase (AP) promoters, and could be employed with any promoter system.

New prokaryotic cell cultures are produced upon transformation and culture of host cells using the above method. These cultures comprise (a) mature eukaryotic protein and (b) a direct hybrid fusion protein of the mature eukaryotic protein with a prokaryotic secretion signal sequence. Ordinarily, greater than about 25 percent, generally up to about 90 percent, of the total weight of mature and fusion protein is mature protein located in the periplasm of the cell.

Brief Description of the Drawings

FIG. 1 discloses the STII gene, including its translated and untranslated regions. The principal portion of its S.D. sequence is overlined at nucleotides 155–161. The imputed amino acid sequence for the STII signal is located at residues -23 to -1 and for the mature STII enterotoxin at residues 1–48. FIG. 1 also discloses the processing site for STII (designated "cleavage site") and various restriction enzyme sites. The asterisk designates the likely mRNA synthesis initiation site assuming that the STII promoter includes the overlined structures at position 84–89 and 108–114.

FIG. 3 is a detail of the plasmid trp-STII-hGH.

FIG. 3a is the nucleotide sequence of the trp promoter region, STII signal and the hGH gene in ptrp-STII-hGH.

FIG. 5 is the nucleotide sequence of the AP promoter region, STII signal and the hGH gene in pAP-STII-hGH.

FIG. 6 is the nucleotide sequence of the AP promoter region, the AP signal and the hGH gene in pAP-1.

Detailed Description

Figure 2A:
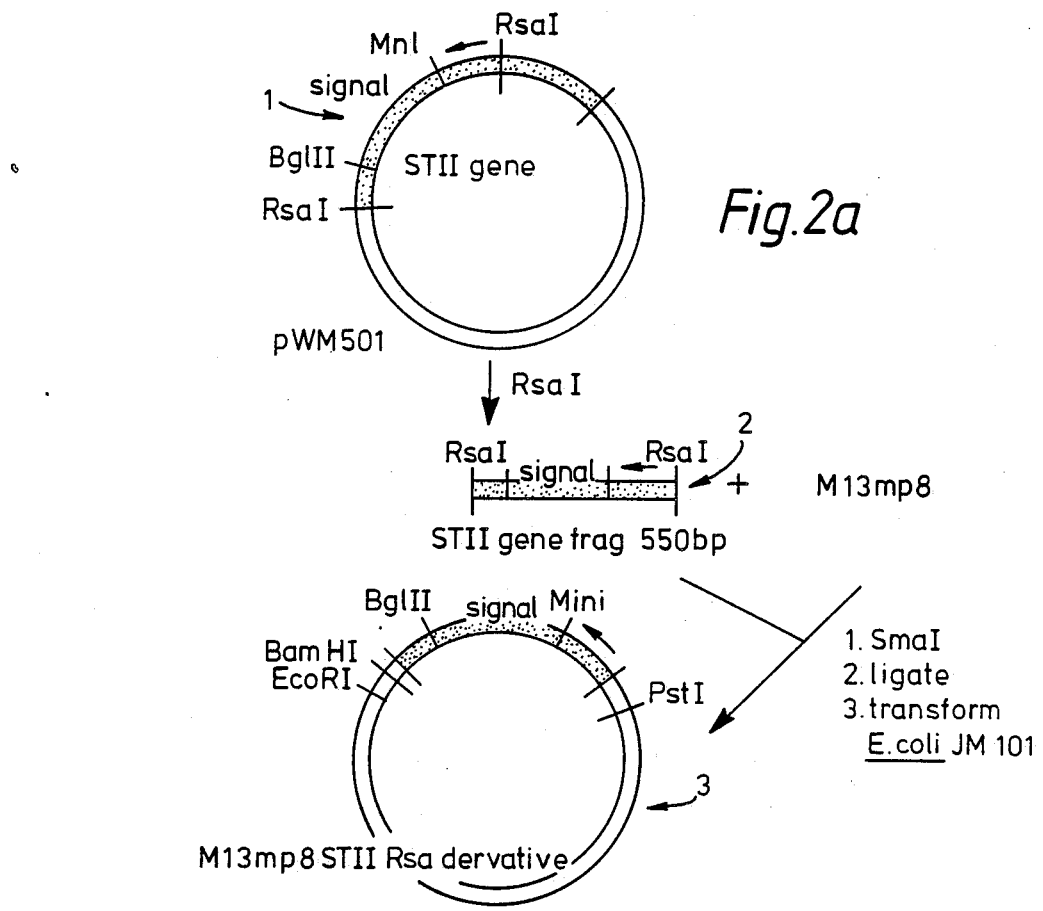
FIGS. 2a–2d disclose the construction of a vector (ptrp-STII-hGH) encoding a secretable STII-hGH fusion protein under the control of the trp promoter and containing an STII S.D. sequence.
Figure 2A:
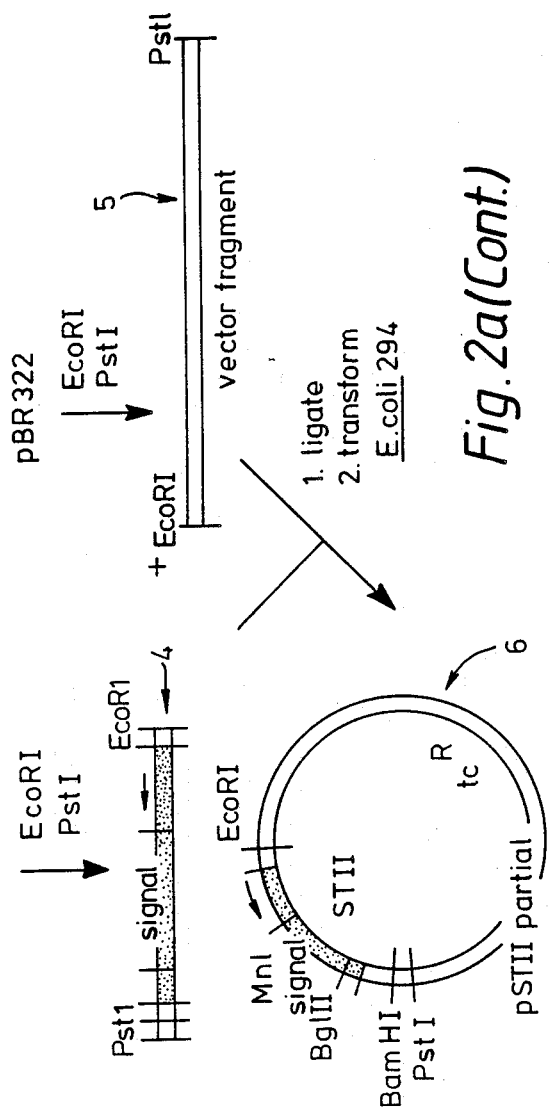

Applicants have demonstrated the secretion of direct hybrid fusions of a prokaryotic signal and desired eukaryotic protein, notwithstanding the complexity of the host vector systems at both the level of preprotein synthesis and secretion. Plasmids were constructed in which the trp or AP promoters were employed with various directly linked prokaryotic signal and eukaryotic protein sequences. Suitable hosts were transformed with each of these plasmids and the amount and distribution of product between the periplasm and cytoplasm determined. These experiments demonstrated that mature eukaryotic proteins are secreted and correctly processed into the periplasmic space of organisms from direct hybrid fusion proteins. The following table shows the results of successful experiments. The results obtained by using the normal hGH eukaryotic signal are shown for comparison.

TABLE 1

Effect of Promoters and Signal Peptides on Expression and Secretion of Eukaryotic Proteins

| Promoter | Signal | Gene | Host | Locations/ Levels[3] | Processing[4] | Media |
|---|---|---|---|---|---|---|
| trp | STII | hGH | 294 or W3110[8] | 90 percent periplasmic; 1 gram | correct | defined or LB |
| AP | STII | hGH | W3110 | 50 percent periplasmic; 0.5 gram | correct | defined-pi[1] |
| AP | AP | hGH | 294[2] | 90 percent periplasmic; 0.1 gram | correct | LB-pi |
| trp | hGH | hGH | 294 or W3110 | 90 percent periplasmic; 50 mg | correct | defined/ LB |
| trp | STII | hLIF-A[6] | 294 | 50 percent periplasmic; 1.9 mg | correct | LB |
| trp | STII | mIgG-K[7] | 294 | 60 percent periplasmic; ND | ND[5] | LB |

[1]inorganic phosphate depleted medium
[2]E. coli ATCC 31446
[3]Variation is typically encountered among experiments. Relevant parameters include culture density, the time at which secreted protein is recovered, and other variables. The total amount of mature and fused eukaryotic protein, as well as the periplasmic percentage, must be considered approximate. The levels are reported as grams/50 equivalent culture OD units at 550 nm/liter. Cultures were grown in 10 or 20 ml fermentations in shake flasks.
[4]Correct processing means that the secreted protein exhibited the same amino terminus as is found when the protein is isolated from natural sources.
[5]ND means not done.
[6]human leukocyte interferon-A
[7]The light chain of a murine monoclonal anti-CEA immunoglobulin.
[8]E. coli ATCC 27325

Applicants' initial attempts to secrete some mature eukaryotic proteins using prokaryotic signals in the above structural format did not result in synthesis of protein in some cases, and in others expression was not accompanied by secretion. Cultures transformed with vectors for the murine immunoglobulin heavy chain (using the STII signal), human tissue plasminogen activator (using the AP promoter and signal) or a bovine prorennin (using the trp promoter and the STII signal in E. coli hosts), or hGH (using the Pseudomonas aeruginosa enterotoxin A signal) synthesized very low or undetectable quantities of either the preprotein or secreted mature protein. Other transformed cultures failed to process STII signal fusions with bovine gamma interferon, prorelaxin, interleukin-2 or bovine prorennin. These results were obtained in limited and preliminary experiments.

It is clear from this work that direct hybrid fusions of prokaryotic signals with mature eukaryotic proteins are recognized by bacterial cells, i.e., processed and transported into the periplasm. Given that knowledge, the skilled artisan must nonetheless exert diligence in identifying functional constructions.

This effort should be directed first at screening vectors encoding direct hybrid fusions with signals obtained from a variety of periplasmic bacterial proteins, e.g. enzymes or enterotoxins. If the secretion of mature eukaryotic protein is not obtained upon the transformation and culture of E. coli with such constructions then other genera of gram negative bacteria should be screened for the ability to secrete the mature protein. Lastly, the signal peptide may be mutated in order to enhance or modify its processing characteristics.

The method herein is facilitated by the ability of gram negative bacteria to recognize direct fusions with the STII enterotoxin signal peptide. Furthermore, it is based on the additional discovery that elevated yields are obtained by use of the STII S.D. sequence.

Partial amino acid sequences for hGH and STII enterotoxin preproteins are shown below with the starting amino acid for each mature protein being underlined.

hGH . . . leu gln glu gly ser ala phe pro ala met ser leu . . .

STII . . . ala thr asn ala tyr ala ser thr gln ser asn lys . . .

As can be seen, virtually no homology whatever exists between these two sequences in the vicinity of their signal cleavage sites. Thus it was surprising that the host cells were able to recognize the STII-hGH hybrid junction and process the STII-hGH preprotein correctly and secrete hGH.

The prokaryotic signal sequence to be used herein is the signal sequence from any bacterial secreted or cell membrane protein, or mutation thereof. Examples of suitable signals are those associated with hydrolases, phosphatases, proteases, antibiotic resistance enzymes, e.g. beta lactamase, binding proteins such as MalE (maltose binding protein) and enterotoxins. The beta lactamase signal is not preferred. The preferred embodiments are found among the heat stable (ST) and heat labile (LT) enterotoxins of E. coli. Of the ST enterotoxins, STII is most preferred.

According to Picken et al., op cit, the STII signal polypeptide was either the amino acid sequence NH$_2$-met lys lys asn ile ala phe leu leu ala ser met phe val phe ser ile ala thr asn ala, or this sequence with an additional carboxyl-terminal tyr ala. In fact, E. coli cleaves the signal after tyr ala. Thus, the STII signal DNA which is used in the vectors further described herein will encode the tyr ala alternative.

The prokaryotic signal may be mutated in order to increase the proportion of eukaryotic protein that is secreted. Generally, mutations in codons encoding amino acid positions outside of the hydrophobic core of the signal, e.g., residues -1, -2 or -3, are more likely to exert a significant effect on signal cleavage. The mutated DNA will express an amino acid at the site of mutation which is different from the wild type signal. Most conveniently a plurality of codons are substituted at a given position, each of which encodes a different amino acid. This is accomplished by methods known in the art. For example see S. Michaelis, op. cit., as applied to the alkaline phosphotase signal. Each individual construction then is ligated to DNA encoding the mature human protein in an expression vector, the vector used to transform hosts, the transformants cultured and the secretion level determined for each mutant as is more fully described below. Transformants that secrete optimal levels of desired protein are identified and the responsible constructions selected. With respect to the STII signal, it is expected that amino acid substitutions in the hydrophobic region (residues -5 to -17 in FIG. 1) will not adversely affect the signal efficacy so long as the substituted amino acids are uncharged and, preferably, hydrophobic. Also, deletions or insertions of one or two like residues in this region are acceptable. The most sensitive region of the leader is residues -1 and -21 to -22 (FIG. 1). Mutations in these residues, including insertions or deletions generally are deleterious, but occasionally beneficial effects on yield or secretion are obtained. Mutations that are so extensive as to convert the expressed signal to the eukaryotic signal ordinarily associated with the desired protein or other eukaryotic proteins are not prokaryotic signal mutations as defined herein.

Mutagenic optimization is particularly desirable upon switching from one host to another while using vectors containing substantially the same signal. The reason for this is that allelic variants in the bacterial enzyme system responsible for cleaving the signal-eukaryotic protein fusion and transporting the mature protein may more readily recognize a suitably modified prokaryotic signal.

In accordance with this invention any eukaryotic protein, mutant or derivative may be secreted if proper gram negative hosts and signals are selected, provided of course that the protein per se is capable of being expressed in gram negative hosts. Such eukaryotic proteins include lymphokines, immunoglobulins and hormones. The eukaryotic proteins used herein ordinarily are mammalian proteins such as those of bovine, porcine and human origin. Particularly advantageous results are obtained with growth hormones such as human growth hormone.

Vectors for transforming hosts to express direct hybrid fusion proteins are made in conventional fashion by methods generally known to those skilled in the art. In such vectors, DNA encoding the prokaryotic signal is directly linked to DNA encoding the desired protein. This means that the signal DNA encoding the amino acid immediately upstream from the normal bacterial cleavage site is linked directly to the DNA encoding the first amino acid of the desired mature eukaryotic protein, without any intervening residual sequences from the mature prokaryotic protein or the normal eukaryotic pre sequence. Such direct linkage is accomplished by known methods such as the M13 deletional mutagenesis procedure described in the examples. Alternately, one may chemically synthesize DNA encoding the signal and cleavage region. This DNA is blunt end ligated, or ligated through a convenient restriction enzyme site, to DNA encoding the remainder of the eukaryotic protein.

DNA encoding the alkaline phosphatase or STII signal is directly linked in either fashion to DNA encoding the desired mature eukaryotic protein. When the eukaryotic protein is a growth hormone, the signal will be linked to DNA having as its two first 5' codons, codons which encode at least the first two amino-terminal amino acids of hGH, i.e., NH2–phe pro, and preferably encode the first 15 amino-terminal amino acids of hGH. This sequence ordinarily is part of a DNA sequence encoding growth hormone such as hGH, bovine growth hormone (having the amino-terminal sequence phe pro ala met ser leu) or porcine growth hormone (having the amino-terminal sequence phe pro ala met pro leu) and the allelic variants thereof.

Suitable vectors for use herein are constructed by operably ligating the direct hybrid fusion DNA to replication and translation effecting sequences. Sequences which effect translation of the mRNA include an S.D. sequence present upstream from the prokaryotic signal. Preferably, the S.D. sequence used herein is that of STII, and it is spaced from the prokaryotic signal start codon by the natural intervening sequence (TTTT) found in the STII gene. This construction is obtained most easily by isolating the STII signal complete with its S.D. sequence and normal intervening sequence from a source of the STII gene as is further described below. However, because this portion of the STII gene is only 80 bp long it also is practical to simply synthesize the required sequence by known chemical methods. This is especially preferred if extensive mutagenesis of the signal is contemplated. The construction shown in FIG. 3a contains two S.D. sequences, one upstream S.D. sequence donated by the trp promoter and then the STII S.D. sequence in its normal relationship with the STII signal DNA. We believe that the upstream, non-STII S.D. sequence is not required. Other prokaryotic signal sequences such as the AP signal also may be synthesized by chemical methods as they tend to be less than 100 bp in length.

Transcription of the foregoing S.D.-signal-protein sequence is under the control of a promoter. The promoter is preferably a prokaryotic promoter other than the promoter ordinarily associated with the selected prokaryotic signal. The preferred embodiment is the AP promoter, although others such as the tac, trp or lactose (D. Goeddel et al., "Nature" 281: 544 [1979]) promoters are satisfactory. While these are the most commonly used, other microbial promoters have been discovered and utilized, and details concerning their nucleotide sequences have been published, enabling a skilled worker to ligate them functionally with plasmid vectors (Siebenlist et al., 1980, "Cell" 20: 269). The promoter does not appear to affect the proportion of eukaryotic protein that is secreted. However, it is desirable to screen combinations of promoters and signal sequences for optimal expression since both elements interact in affecting expression levels. For example, compare the results in Table 1 when the STII signal is substituted for the AP signal in combination with the AP promoter.

The promoter-S.D.-signal sequences are present in vectors containing replicon sequences compatible with the host cells. The vectors are generally plasmids rather than phage. They contain a replication site as well as phenotypic marking sequences to facilitate identification of transformed cells. For example, E. coli is typically transformed with a derivative of pBR322, (Bolivar et al., "Gene" 2: 95 [1977]), a plasmid containing genes for ampicillin and tetracycline resistance.

When a DNA sequence is "operably ligated or linked" to another it means that the DNA sequence in question exerts an influence on other DNA sequences. This generally means that the first DNA controls either the transcription or ultimately the translation of the DNA to which it is operably ligated, or affects the processing of the translated protein. For example, a promoter is operably ligated to DNA encoding a preprotein when it affects the rate of translation of the preprotein mRNA. A signal polypeptide is operably ligated to DNA encoding a desired protein when it is placed in reading frame with and ligated directly to the DNA encoding the protein. The term "ligated" in reference to a composition should not be inferred to mean that the composition is only defined in terms of its possible manufacture by ligation. On the contrary, operably ligated elements in a plasmid can be synthesized chemically as a unitary entity.

The host cells that are transformed with the foregoing vectors are bacteria (a) having a periplasmic space between two cell membranes, (b) in which the vector replicates and (c) in which the preprotein is both expressed and processed. The hosts are generally gram negative organisms, particularly Enterobacteriaceae or Pseudomonas and mutants thereof. Host vector systems (hosts transformed with vectors) are preferred in which the promoter controlling expression of the hybrid fusion is constitutively activated or derepressed. A constitutive mutant is one that is capable of secreting a given protein, which here is the promoted direct hybrid fusion and, in some cases, the normally promoted protein, without induction or other changes in culture conditions calculated to derepress or activate the promoter. Either the host cell or the promoter, or both, may be mutated in order for the host-vector system to be constitutively promoted. The promoter used in the vector may be mutated so that it is no longer capable of being repressed by a repressor protein. Such mutations are known. Alternatively, the host cells are mutated to become constitutive for proteins under the control of a wild-type or unmutated promoter. Such hosts are conveniently prepared by transduction from publically available strains containing the mutant alleles. Preferably, host cells transformed with AP promoter-bearing vectors carry a phoT or phoR mutant allele. The former is a disabling mutant believed to be in the gene encoding a phosphate ion transport protein. The phoR mutant is a disabling mutant in the gene encoding a repressor protein. These mutant alleles are widely known and available in the art and may be transferred into hosts by known techniques. Surprisingly, the constitutive hosts processed a greater percentage of the expressed product than the wild type hosts which were induced by phosphate depletion.

The host cells may, but need not constitutively express the host protein normally promoted by the promoter used to control transcription of DNA for the direct hybrid fusion. For example, either an *E. coli* phoA deletion mutant, which fails to express active AP, or an AP-synthesizing cell may be used as host; the active secretion of AP by the cells does not necessarily interfere with secretion of the eukaryotic protein. Ordinarily, the host bacterium will be the same species from which the signal was obtained.

While any culture medium ordinarily used for the host cells is satisfactory for the transformants, the composition of host culture medium exerts a strong effect on the secretion of eukaryotic protein by wild type hosts (rather than strain W3110 phoA, phoT or phoA, phoR). Media containing yeast extract results in improved secretion when compared to tryptone (a tryptic digest of casein) or a synthetic mixture of 19 amino acids. It appears that one or more components of yeast extract helps to activate secretion.

In order to simplify the Examples certain frequently occurring and well-known methods employed in recombinant constructions will be referenced by shorthand phrases or designations.

Plasmids are designated by a lower case p preceded and/or followed by capital letters and/or numbers. The starting plasmids or sources of DNA herein are commercially available, are publically available on an unrestricted basis, or can be constructed from available plasmids or polynucleotides in accord with published procedures. In addition, other equivalent plasmids are known in the art and will be apparent to the ordinary artisan since the plasmids generally only function as replication vehicles for the preprotein and its control sequences, or for elements thereof in intermediate constructions.

"Digestion" of DNA refers to catalytic cleavage of the DNA with an enzyme that acts only at certain locations in the DNA. Such enzymes are called restriction enzymes, and the sites for which each is specific is called a restriction site. "Partial" digestion refers to incomplete digestion by a restriction enzyme, i.e., conditions are chosen that result in cleavage of some but not all of the sites for a given restriction endonuclease in a DNA substrate.

The various restriction enzymes used herein are commercially available and their reaction conditions, cofactors and other requirements as established by the enzyme suppliers were used. Restriction enzymes commonly are designated by abbreviations composed of a capital letter followed by other letters and then, generally, a number representing the microorganism from which each restriction enzyme originally was obtained. In general, about 1 $\mu$g of plasmid or DNA fragment is used with about 1 unit of enzyme in about 20 $\mu$l of buffer solution. Appropriate buffers and substrate amounts for particular restriction enzymes are specified by the manufacturer. Incubation times of about 1 hour at 37° C. are ordinarily used, but may vary in accordance with the supplier's instructions. After incubation, protein is removed by extraction with phenol and chloroform, and the digested nucleic acid is recovered from the aqueous fraction by precipitation with ethanol. Digestion with a restriction enzyme infrequently is followed with bacterial alkaline phosphatase hydrolysis of the terminal 5' phosphates to prevent the two restriction cleaved ends of a DNA fragment from "circularizing" or forming a closed loop upon ligation (described below) that would impede insertion of another DNA fragment at the restriction site. Unless otherwise stated, digestion of plasmids is not followed by 5' terminal dephosphorylation. Procedures and reagents for dephosphorylation are conventional (T. Maniatis *et al.*, 1982, *Molecular Cloning* pp. 133-134).

"Recovery" or "isolation" of a given fragment of DNA from a restriction digest means separation of the digest on polyacrylamide gel electrophoresis, identification of the fragment of interest by comparison of its mobility versus that of marker DNA fragments of known molecular weight, removal of the gel section containing the desired fragment, and separation of the DNA from the gel, generally by electroelution. This procedure is known generally. For example, see R. Lawn et al., 1981, "Nucleic Acids Res." 9: 6103–6114, and D. Goeddel et al., 1980, "Nucleic Acids Res." 8: 4057.

"Southern Analysis" is a method by which the presence of DNA sequences in a digest or DNA-containing composition is confirmed by hybridization to a known, labelled oligonucleotide or DNA fragment. For the purposes herein, unless otherwise provided, Southern analysis shall mean separation of digests on 1 percent agarose, denaturation and transfer to nitrocellulose by the method of E. Southern, 1975, "J. Mol. Biol." 98: 503–517, and hybridization as described by T. Maniatis et al., 1978, "Cell" 15: 687–701.

"Transformation" means introducing DNA into an organism so that the DNA is replicable, either as an extrachromosomal element or chromosomal integrant. Unless otherwise provided, the method used herein for transformation of E. coli is the CaCl$_2$ method of Mandel et al., 1970, "J. Mol. Biol." 53: 154.

"Ligation" refers to the process of forming phosphodiester bonds between two double stranded nucleic acid fragments (T. Maniatis et al., Id., p. 146). Unless otherwise provided, ligation may be accomplished using known buffers and conditions with 10 units of T4

DNA ligase ("ligase") per 0.5 μg of approximately equimolar amounts of the DNA fragments to be ligated.

"Preparation" of DNA from transformants means isolating plasmid DNA from microbial culture. Unless otherwise provided, the alkaline/SDS method of Maniatis et al., Id. p. 90., may be used.

"Oligonucleotides" are short length single or double stranded polydeoxynucleotides which are chemically synthesized by known methods and then purified on polyacrylamide gels.

All literature citations are expressly incorporated by reference.

EXAMPLE 1

Construction of a Plasmid Encoding for the E. coli Heat-Stable Enterotoxin (STII) Gene Signal Peptide Sequence.

The following construction is illustrated in FIG. 2a. The plasmid pWM501 (Picken et al, op cit) contains the heat-stable enterotoxin (STII) gene. A portion of the DNA which encodes the STII gene was recovered from pWM501 1 (stippled region of FIG. 2a) using the following steps. pWM501 was digested with RsaI and the 550 bp DNA fragment 2 was isolated. This gene fragment was ligated to the phage M13mp8 (J. Messing et al. in the *Third Cleveland Symposium on Macromolecules: Recombinant DNA*, Ed. A. Walton, Elsevier, Amsterdam (1981) pp 143-153) that had been previously digested with SmaI. The ligated DNA was used to transform *E. coli* JM101, a commercially available strain for use with the M13 phage. Clear plaques were recovered. The double stranded M13mp8 STII Rsa derivative 3 was isolated from an *E. coli* JM101 infected with this phage using standard procedures (J. Messing et al. op cit). By the use of the M13mp8 subcloning procedure just described the approximately 550 base pair fragment 2 containing the STII leader gene is now bounded by a series of different restriction endonuclease sites provided by the phage. The M13mp8 STII Rsa derivative 3 then was digested with EcoRI and Pst I and a DNA fragment 4 slightly larger than fragment 2 was isolated.

EcoRI-PstI fragment 4 was subcloned into pBR322. This was accomplished by digesting pBR322 with EcoRI and PstI and isolating the vector 5. The isolated vector 5 was ligated to the EcoRI-PstI DNA fragment 4. This DNA mixture was used to transform *E. coli* 294 and tetracycline resistant colonies selected A plasmid 6 was isolated from a resistant *E. coli* colony and designated pSTII partial

EXAMPLE 2

Construction of a Plasmid encoding the STII Signal Peptide Under the Control of the Trp Promoter.

Figure 2B:
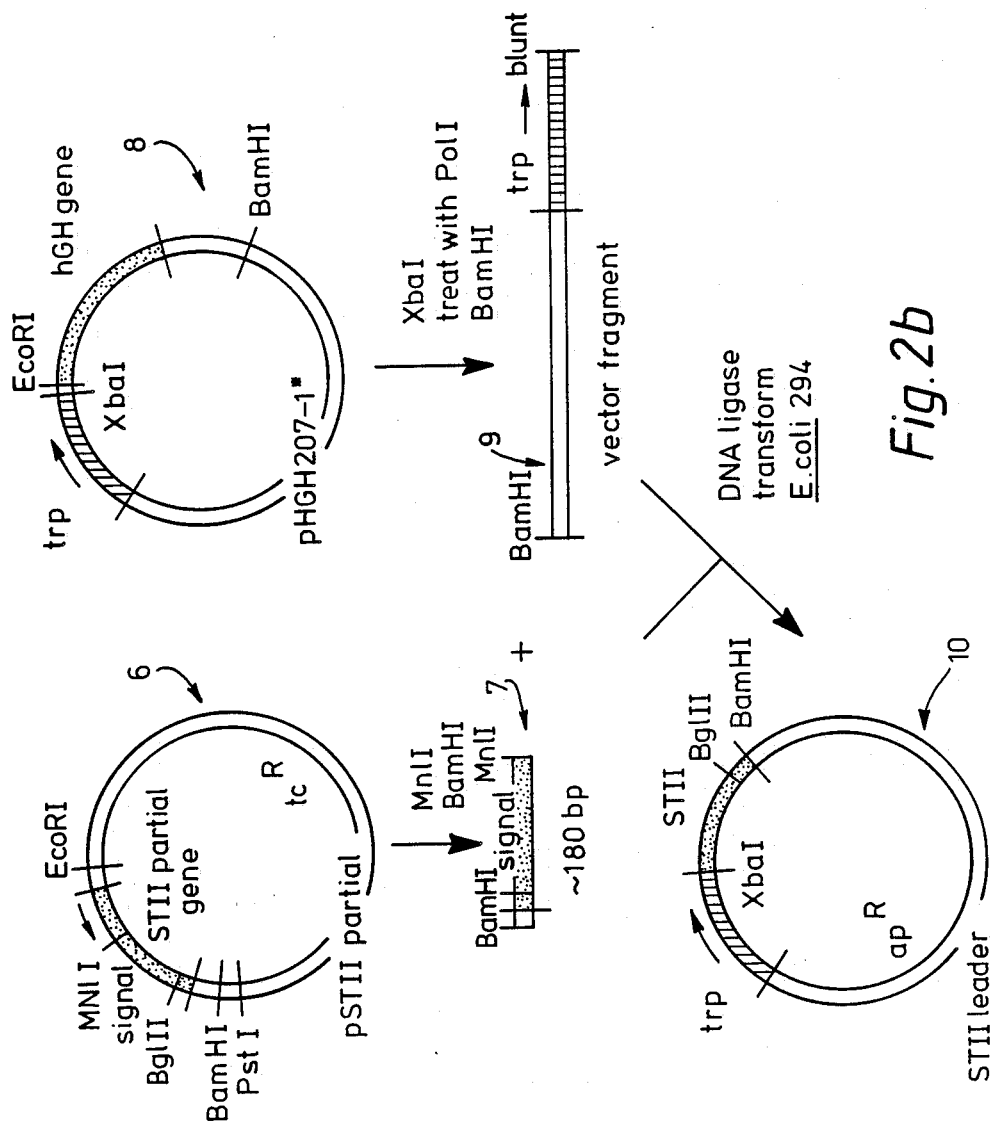

This construction method is shown in FIG. 2b. pSTII partial from Example 1 was digested with MnlI and BamHI and a 180 bp fragment 7 containing the STII S.D. sequence, the STII signal sequence, and the first 30 codons of the mature STII gene was isolated. DNA fragment 7 was ligated to a plasmid containing the trp promoter. One such plasmid pHGH207-1, 8, has been described previously (H. de Boer et al., 1982, in: *Promoters: Structure and Function*, Eds. R. Rodreguez et al. Chamberlin, Praeger Pub., New York, N.Y., pp 462-481). A derivative of this plasmid, pHGH207-1*, wherein the EcoRI site 5' to the trp promotor had been converted to EcoRI* by filling in with DNA polymerase I (DNA pol I) and joining the blunt ends by ligation (S. Cabilly et al., 1984, "Proc. Natl. Acad. Sci. USA" 81: 3273-3277) was used in this example. The trp promoter-containing plasmid was digested with XbaI and treated with DNA pol I and all four dNTPs to fill in the protruding sequence. The DNA preparation was then digested with BamHI and the vector containing fragment 9 isolated. Vector fragment 9 then was ligated to the 180 bp STII signal-containing DNA fragment 7 isolated above. The ligation mixture was used to transform *E. coli* 294 to ampicillin resistance. A plasmid designated STII leader 10 was isolated from an ampicillin resistant colony. This plasmid contains the STII signal sequence and a portion of the gene encoding mature STII under the control of the trp promoter. In the following example, the DNA sequence encoding mature hGH was operably ligated downstream from the trp - STII signal sequence.

EXAMPLE 3

Construction of an Expression and Secretion Plasmid for hGH

Figure 2C:
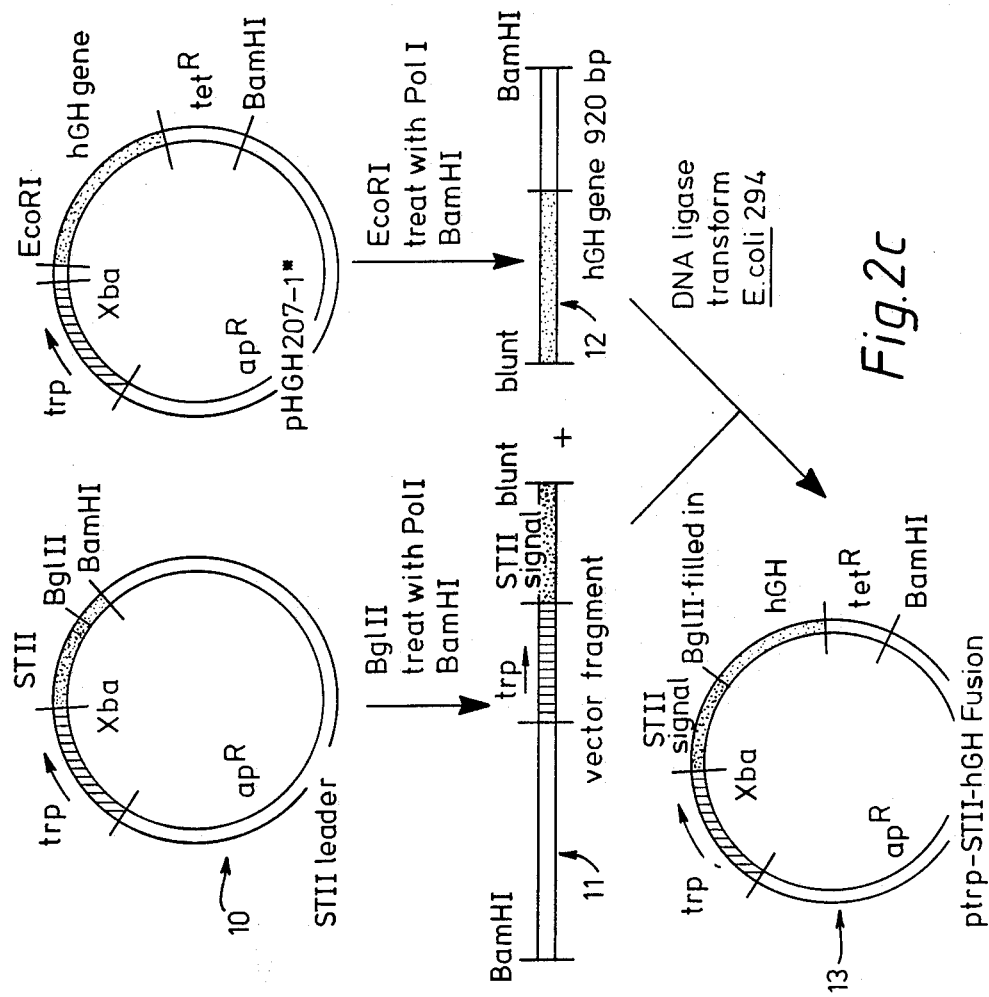
Figure 2D:
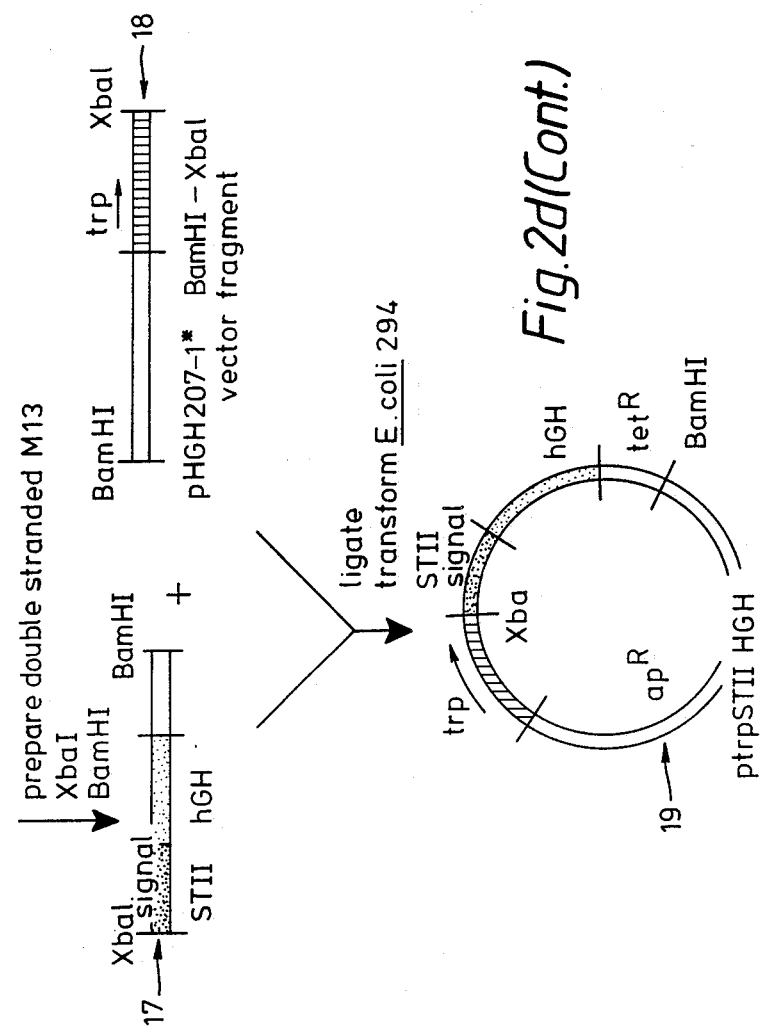

Refer to FIGS. 2c-2d for a schematic display of this method. STII leader 10 was digested with BglII then treated with DNA pol I and all four NTP's to fill in the protruding end, and then digested with BaaHI. The vector-containing fragment 11 was isolated. The plasmid pHGH207-1* from Example 2 was digested with EcoRI, treated with DNA pol I and all four NTP's to fill in the protruding end, and then digested with BamHI. The hGH gene-containing fragment 12 of about 920 bp was isolated from the BamHI digestion. These two fragments were ligated and the DNA mixture used to transform *E. coli* 294 to tetracycline resistance. A plasmid designated ptrpSTII-HGH-fusion 13 was isolated from the resistant *E. coli* colonies. This plasmid still contains extraneous nucleotides encoding a portion of the STII mature protein between the STII leader peptide sequence and the hGH structural gene. These nucleotides were deleted using the M13 site specific mutagenesis procedure (J.P. Adelman et al, 1983, "DNA" 2: 183-193).

The gene from ptrpSTII HGH fusion 13 was incorporated into the single stranded phage M13mp10 (J. Messing et al., op cit. and J. Adelman et al. op cit.). M13 mutagenesis phage and *E. coli* strains are commercially available. Mutagenesis was accomplished first by digesting plasmid 13 with XbaI and BamHI and then recovering fragment 14. M13mp10 was digested with XbaI and BamHI and the phage fragment (not shown) was isolated. Fragment 14 was ligated into the phage fragment and the ligation mixtures used to transform JM101. The transformed culture was plated and incubated. Phage having the fragment 14 insert were identified as clear rather than blue plaques in the *E. coli* chromogenic indicator lawn. Corresponding phage were grown on *E. coli* JM101, and the culture centrifuged. Single stranded phage 15 are present in the supernatant. Single stranded phage 15 DNA was prepared, annealled to the synthetic oligonucleotide primer 5'pCAAATGCCTATGCATTCCCAACTATACC-OH3', primer extended with DNA pol I and the four NTPs to obtain double stranded DNA (one of which strands contained the deletion), treated with T4 ligase, extracted and used to transform *E. coli* JM101 (See J. Adelman et al., op cit). Note that the first 14 nucleotides of the primer are the coding sequence for the 3' end of the STII signal, while the last 14 nucleotides are the coding sequence for the 5' end of the mature hGH gene. Double stranded phage were obtained from the cellular contents of the transformed JM101, transfected into plated E. coli JM101, transfer filter impressions taken of the plates and double stranded phage containing the deletion were identified on the filters by Southern analysis with a 5'-32P-labelled obigonucleotide having the DNA sequence of the primer. Double stranded DNA 17 was prepared from the E. coli infected with the M13mp10 containing the gene deletion. This DNA was digested with XbaI and BamHI and the DNA fragment 17 isolated. This was ligated in the presence of fragment 18 from similarly digested and isolated pHGH207-1*. The ligation was used to transform E. coli 294 to tetracycline resistance. Plasmid ptrp-STII-HGH 19 was recovered and its nucleotide sequence determined. A detailed restriction map of this plasmid is shown in FIG. 3. The DNA sequence of this plasmid in the vicinity of the hGH gene is shown in FIG. 3a.

EXAMPLE 4

Expression and Secretion of hGH

HGH was synthesized in shake culture using plasmid 19 from Example 3. E. coli 294 was transformed with plasmid 19 and innoculated into 10–20 ml of LB medium with 5 μg/ml tetracycline in a 50 or 125 ml shake flask. The flask was cultured for 12–24 hours at 37° C. without the addition of any further medium, after which the cells were recovered by centrifuging. Total cellular hGH was assayed by radioimmunoassay of sonicated cells. The secreted hGH was recovered through osmotic shock and determined to be mature hGH by SDS-PAGE and N-terminal amino acid terminal sequencing. Amounts recovered were about ten times that which is expressed when using the human hGH signal under control of the trp promoter.

EXAMPLE 5

Construction of Plasmid pAP-1 Designed to Express and Secrete Human Growth Hormone (hGH) Under the Control of the AP Promoter and Signal Sequence.

Figure 4A:
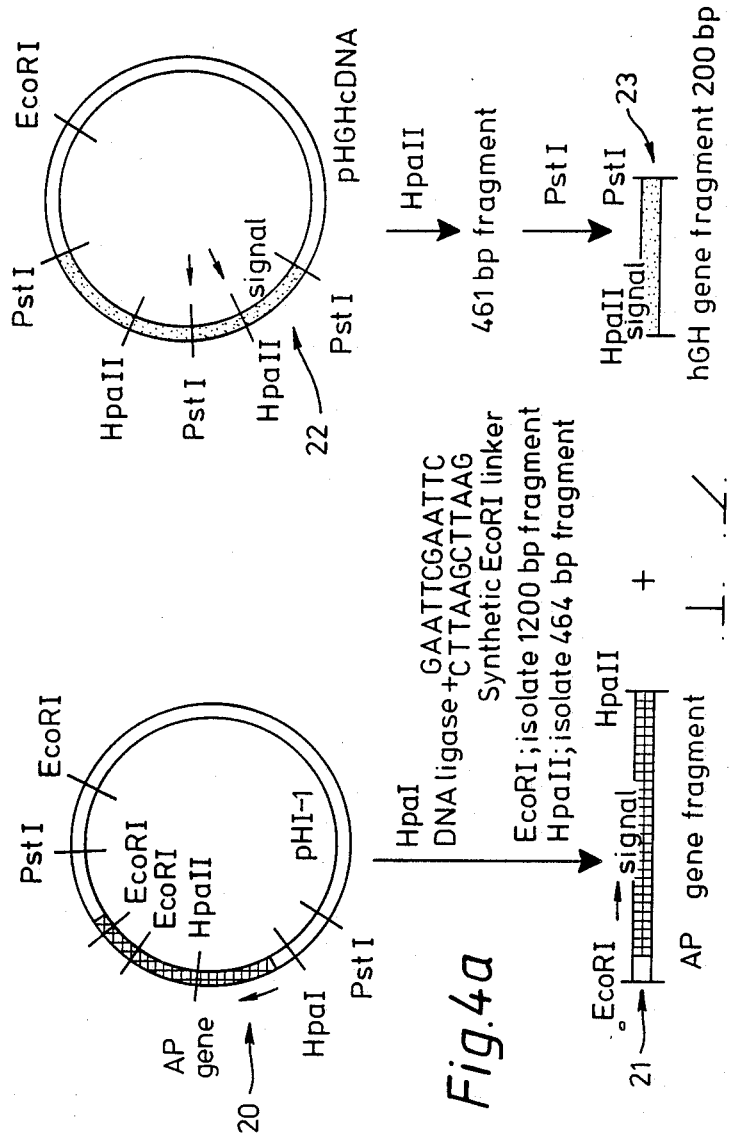
FIGS. 4a–4c disclose the construction of the vectors pAP-1 and pAP-STII-hGH encoding secretable AP-hGH and STII-hGH fusion proteins under the control of the AP promoter, the vector encoding the latter containing an STII S.D. sequence.
Figure 4B:
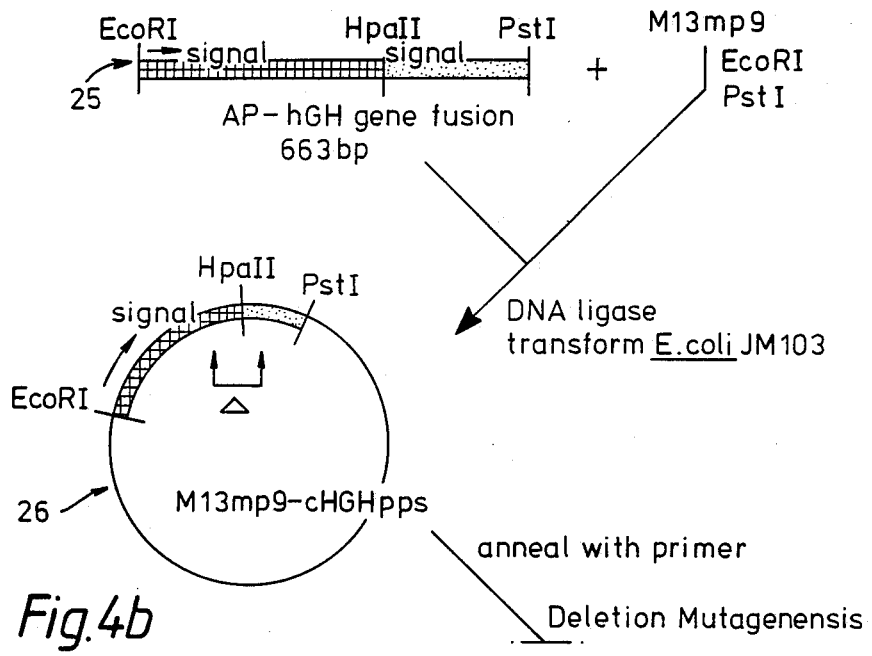
Figure 4B:
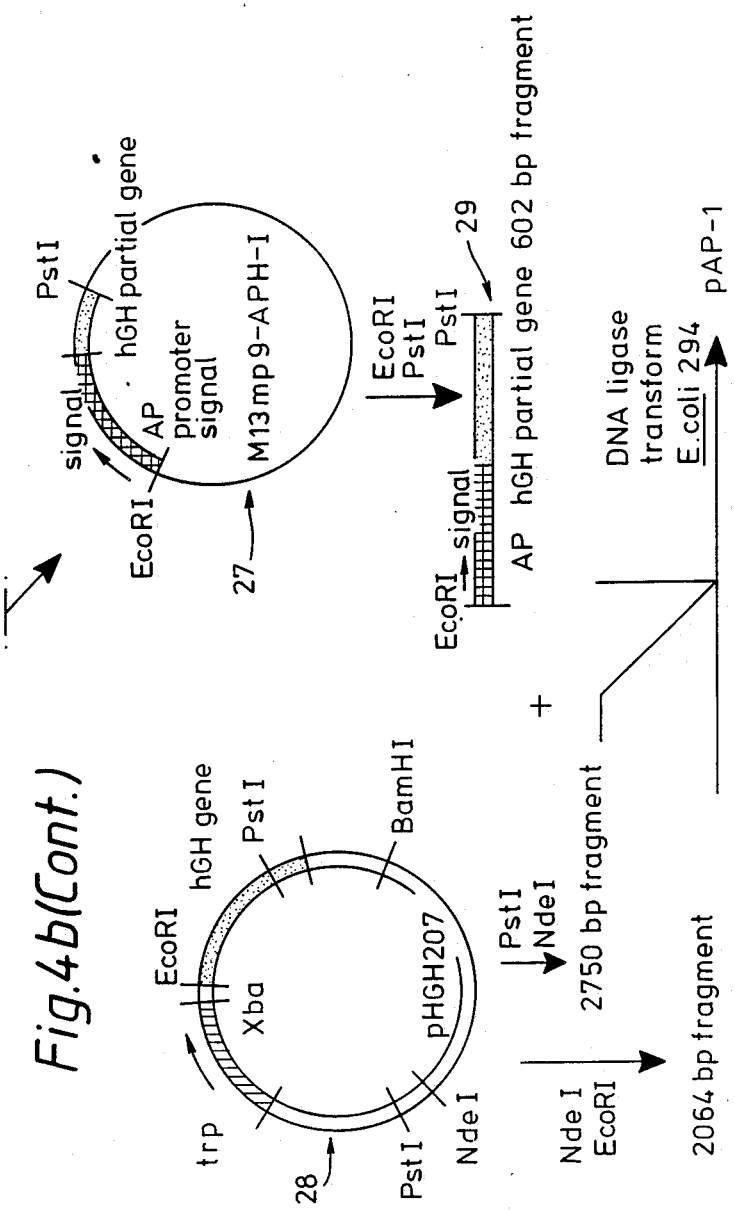
Figure 4C:
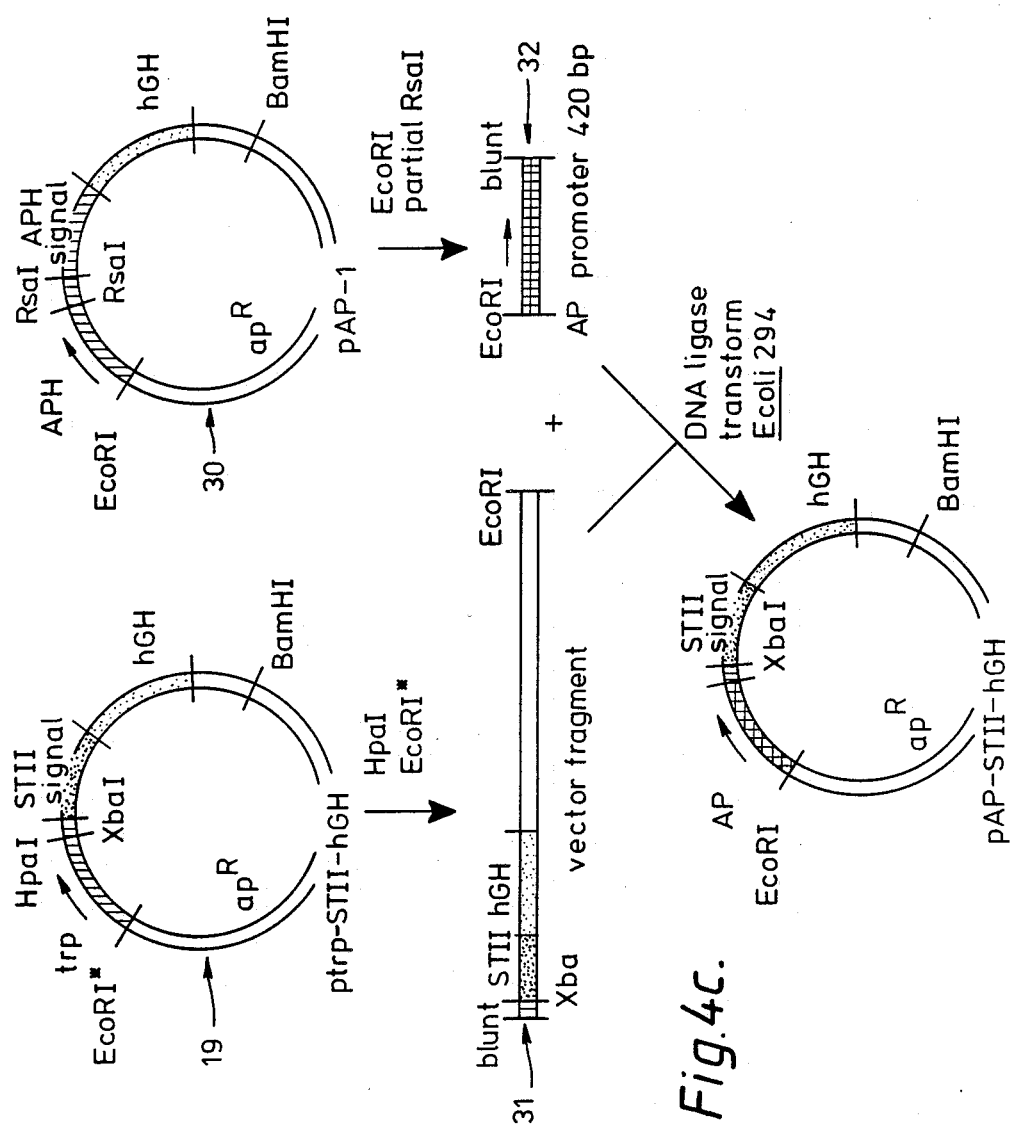

This construction is shown in FIGS. 4a–4c. A DNA fragment containing a portion of the AP gene was isolated from the plasmid pHI-1 20 [Inouye, H., et al., J. Bacteriol. 146: 668–675 (1981)]. This was done using a series of steps to introduce an EcoRI site 5' to the AP gene and promoter sequence. The plasmid 20 was digested with HpaI and then ligated to a linker molecule containing two EcoRI sites in tandem. After heat inactivation of the ligase enzyme the DNA was digested with EcoRI and a 1200 bp fragment isolated. This DNA fragment was then treated with HpaII and a 464 bp fragment 21 isolated. A plasmid 22 containing cDNA prepared from human growth hormone mRNA was prepared as described by Martial et al., "Science" 205: 602–606 (1979) and Roskem et al., "Nucleic Acids Res." 7: 305–320 (1979) (see also European Patent Application No. 84302725.1). Plasmid 22 was digested with HpaII and a 461 bp fragment was isolated. The 461 bp fragment was further digested with PstI and a 200 bp fragment 23 containing part of the hGH gene then isolated. DNA fragments 21 and 23 were ligated to a 3609bp DNA fragment isolated from pBR322 that had been previously digested with EcoRI and PstI. This DNA ligation mixture was used to transform E. coli 294 to tetracycline resistance. A plasmid 24, designated pcHGHpps, was recovered from a transformant colony.

In plasmid 24 the gene encoding the AP promoter and signal sequence in pcHGHpps was linked to hGH in the same reading frame. However a number of extraneous nucleotides were present between the signal sequence and the beginning of the mature hGH gene. This extraneous nucleotide sequence was deleted by mutagenesis. pcHGHpps was digested with EcoRI and PstI and the 663 bp fragment 25 isolated. Fragment 25 was introduced into M13mp9 previously digested with PstI and EcoRI. This was ligated and used to transform E. coli JM101. Clear plaques were selected and a derivative phage 26, M13mp9-cHGHpps, was identified and isolated. Phage 26 was annealed to the synthetic oligonucleotide primer 5'PCTGTGACAAAAGCCTTC-CCAACCATTCC-OH3'. The first 14 nucleotides correspond to the sequence of the 3' end of the AP signal peptide and the last 14 correspond to the 5' end of the mature hGH coding sequence. The site-specific deletion mutagenesis was performed as previously described in Example 3 (see also J. Adelman et al. op cit.). Plaques containing the desired deletion were detected by Southern analysis with the 5'-32P-labeled oligonucleotide primer of this Example. Without enrichment for the desired genotype, nine percent of the plaques screened hybridized to the labelled primer. One of the positives, M13mp9-AP-1, 27, was determined by the dideoxy chain termination nucleotide sequencing method to have the expected sequence. The partial hGH gene, now correctly fused to the AP promoter and signal gene, was introduced into pHGH207, 28 (H. de Boer et al., qp cit). This was accomplished by digesting pHGH207 with PstI and NdeI, and then isolating the 2750 bp fragment. Another sample of pHGH207 was digested with NdeI and EcoRI and a 2064 bp fragment isolated. The M13mp9-AP-1 phage was digested by EcoRI and PstI, and the 602bp AP hGH partial gene 29 was isolated. The 2750 and 2064 bp fragments were ligated in a three-part ligation with fragment 29, and the ligation mixture then used to transform E. coli 294 to ampicillin resistance. pAP-1 was isolated from a resistant colony and characterized by restriction enzyme mapping and nucleotide sequence analysis.

EXAMPLE 6

Construction of a Plasmid (pAP-STII-hGH) to Express and Secrete hGH Under the Control of the AP Promoter ptrp-STII-hGH (from Example 3) was digested with HpaI and EcoRI and the vector fragment 31 isolated. A 420 bp AP promoter fragment 32 was isolated from the plasmid pAP-1 after digestion with EcoRI and partial digestion with RsaI. Fragments 31 and 32 were ligated and used to transform E. coli 294 to ampicillin resistance. The plasmid pAP-STII-hGH was isolated and characterized by restriction enzyme mapping and nucleotide sequence analysis. The nucleotide sequence and translated amino acid sequence of the AP-STII-hGH construction is shown in FIG. 5.

EXAMPLE 7

Recovery of hGH from E. coli Containing the Plasmid pAP-STII-hGH.

E. coli W3110 and 294 were transformed respectively with pAP-STII-hGH or pAP-1 and cultured as described in Example 4 except that the medium used was phosphate depleted. The amounts synthesized and the distribution of processed and unprocessed hGH were determined as described in Example 4. The results are described in Table 1. In small volumes ptrp-STII-hGH produces better results, as can be seen from Table 1, but in 10 liter culture volumes the preferred embodiment is the plasmid pAP-STII-hGH since AP promoted cells can grow to higher densities than trp promoted organisms.

EXAMPLE 8

Large Volume Fermentation and hGH Recovery

Eight hours prior to the start of a 10 liter fermentation a 500 ml inoculum culture is grown up. A transformant of *E. coli* W3110 (tonA, phoA, phoT) (Example 9) containing pAP-STII-hGH is inoculated into a sterile 2 liter flask containing 500 ml of LB medium and tetracycline (0.5 µg/ml). The culture is incubated in a rotary shaker at 37° C. for eight hours. A sterile 10 liter fermentation medium is prepared, containing the following ingredients: 26g $K_2HPO_4$, 13g $NaH_2PO_4 \cdot 2H_2O$, 15g KCl, 50g $(NH_4)_2SO_4$, 10g $Na_3$ citrate, 50 ml of 50 percent glucose, 1000 ml of 10 percent NZ-amine YT, 100 ml of IM $MgSO_4$, 5 ml of 2.7 percent $FeCl_3$, 5 ml of trace metals, 1 ml of 5 mg/ml tetracycline, 5 ml of antifoaming agent, and 6.5 liters of $H_2O$. The starting pH of the medium is titrated to 7.5 by adding $H_2SO_4$, and the run is begun by seeding the 500 ml inoculum culture into the 10 liter fermenter. Throughout the run the temperature is maintained at 37° C. and the culture agitated under aeration. From the outset, the cells are fed glucose (50 percent) at a flow rate of 0.5 ml/min. When the OD 550 is in the range 10–25 the glucose feed rate is manually adjusted to keep the pH at 7.5 and the residual glucose level $\leq \frac{1}{4}$ percent. When the OD 550 reaches 25, the glucose feed rate is manually adjusted to drive the $dO_2$ level to 30 percent and thereafter, the glucose feed rate is periodically adjusted to maintain the $dO_2$ level at 30 percent. Thirty-six hours after the start of fermentation the cells are killed and harvested.

The glucose feed and aeration are turned off but the agitation rate of 650 rpm is maintained. 1-butanol is added immediately to the fermenter to yield a final concentration of 1.5 percent and steam is immediately injected into the fermenter jacket so that the temperature in the tank rises rapidly to 50° C. When the temperature reaches 50° C., it is held at this temperature for 10 minutes. Then the fermenter is rapidly cooled below 20° C. and the cellular contents of the fermenter are harvested by centrifugation. The cell paste is first frozen at −20° C. and then transferred to a −80° C. freezer.

The cell paste, frozen at −80° C., is thawed overnight at 4° C. and all subsequent steps are performed at 4° C. The paste is mixed in 4 volumes of 10mM Tris-HCl,pH=8.0 and suspended in an Ultra-Turrex homogenizer for 30 seconds. The suspension is stirred for 30 minutes and then the cells are removed by centrifugation at 12,000×g for 30 minutes. The periplasmic proteins contain in the supernatant mature hGH at between 0.5 and 1 gram/liter/100 $OD_{550}$ with about 95 percent of the total hGH (as estimated from immunoblots with peroxidase-coupled anti-hGH) in processed form in the periplasm. About 50–60 percent of the total cellular hGH is recovered in the supernatant. The supernatant contains about 20 percent hGH by weight of protein.

EXAMPLE 9

Construction of a Host Organism W3110 tonA, phoA, phoT

The host organism for the fermentation was constructed in several steps using standard techniques involving transductions with phage derived from PI (J. Miller, *Experiments in Molecular Genetics*). The phoT and phoA mutations were sequentially cotransduced from *E. coli* into strain W3110 tonA with the aid of genetically linked antibiotic-resistance transposons. The presence of the phoT mutation, which was introduced first, was recognized since these transductants form blue colonies on high phosphate, phosphochromogen-containing plates (5-bromo-4-chloro-3-indoylphosphate). The introduction of the phoA mutation was recognized as transductants which form white colonies on low phosphate, phosphochromogen plates. This phoT mutant, or a phoR mutant constructed in similar fashion, when transformed with pAP-STII-hGH, secretes over 90 percent of the total hGH into the periplasmic space over the course of the fermentation. In contrast, a non-constitutive bacterium such as W3110 only secretes about 50 percent of the hGH into the periplasm and total expression levels are somewhat lower in some cases. The presence or absence of the phoA mutant makes little or no difference in the yield of heterologous protein. However, since phoA mutants do not secrete AP, it is not necessary to separate AP in the course of purifying periplasmic hGH from phoA mutants.

We claim:
1. A DNA sequence encoding a protein having the sequence of mature hGH, operably linked, at the DNA region encoding the amino terminus of hGH, to a DNA sequence encoding the STII signal.
2. pAP-STII-hGH.
3. ptrp-STII-hGH.
4. pAP-1.

* * * * *